United States Patent [19]

Marriott, III et al.

[11] Patent Number: 4,654,370

[45] Date of Patent: Mar. 31, 1987

[54] GLYCERYL VALPROATES

[75] Inventors: Thomas B. Marriott, III, Lake Zurich, Ill.; Gerard Y. Paris, Laval, Canada

[73] Assignee: Abbott Laboratories, North Chicago, Ill.

[21] Appl. No.: 112,598

[22] Filed: Jan. 16, 1980

Related U.S. Application Data

[63] Continuation-in-part of Ser. No. 19,814, Mar. 12, 1979, abandoned.

[51] Int. Cl.$^4$ ................... A61K 31/22; C11C 3/02; C07C 67/02
[52] U.S. Cl. ................... 514/547; 260/410.8; 560/263; 514/546
[58] Field of Search ................... 560/263; 260/410.8; 424/311, 312; 514/547, 541

[56] References Cited

U.S. PATENT DOCUMENTS 3,686,238  8/1972  Zaffaroni .................. 260/345.7 R
4,423,071  12/1983  Chignac et al. ................. 424/311

OTHER PUBLICATIONS

Meijer et al, Clinical and Pharmacological Aspects of Sodium Valproate (Epelim) in the Treatment of Epilepsy, Ed. N. J. Legg, published by McS Consultants, 1975, pp. 70-75.
Keil, Z. Physiol. Chem., 282, pp. 137-142 (1947), (Corresponds to Chem. Abstracts, 43:6164-65.)

*Primary Examiner*—Alan Siegel
*Attorney, Agent, or Firm*—Steven F. Weinstock; Martin L. Katz

[57] ABSTRACT

Glycerides esterified with one or two moles of valproic acid and optionally esterified with fatty acids at the remaining hydroxy position(s) have been found to have the same useful therapeutic effect as valproic acid alone but without causing gastric irritation.

25 Claims, No Drawings

GLYCERYL VALPROATES

BACKGROUND OF THE INVENTION

This application is a continuation-in-part of our earlier filed application, U.S. Ser. No. 019,814, filed Mar. 12, 1979, now abandoned.

DETAILED DESCRIPTION OF THE INVENTION

In the last decade, 2-propylpentanoic acid (hereinafter referred to simply as valproic acid) and its sodium salt have been introduced in the arsenal of drugs useful for treating epileptic seizures. Unfortunately, the therapeutic dose for adults is at a level of 1-3 g., an amount that is not easily tolerated by the gastro-intestinal tract of many patients. The potential resulting side effects may manifest themselves in heart-burn, indigestion, abdominal cramps, diarrhea, nausea or even vomiting.

Efforts to overcome these possible side effects have heretofore been unsuccessful. Meijer and Meinardi reported in 1975 that the trivalproyl ester of glycerol showed no adverse side effects. Unfortunately, this ester has substantially no therapeutic value either.

The present invention is directed to compounds of the formula

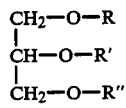

wherein R, R', R and R' or R and R" represent valproyl (i.e., dipropylacetyl) and the remaining substituent or substituents represent hydrogen or a fatty acid acyl radical X—CO— wherein X is an alkyl group of 1–15 carbon atoms with the proviso that when R' is valproyl, R and R" both are represented by X—CO—. The new compounds I show substantially the same anticonvulsant effect as valproic acid, although some of them may have a longer lasting effect. However, the new compounds are essentially devoid of the gastro-intestinal irritation caused in 9–16% of the patients using valproic acid.

The new compounds are prepared by generally known, simple esterification procedures using as one of the starting materials dihydroxyacetone, an epihalohydrin, a labile monoester of glycerol, or isopropylidene glycerol. The present glycerides can also be identified by structures

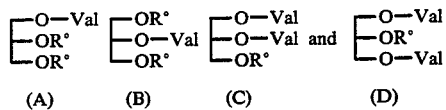

wherein "Val" stands for valproyl and R° is H or X—CO—, except in structure (B) where R° cannot be H. Compounds (B) and (D) can be made by using dihydroxyacetone as the starting material and (B) may further be made by using the diacylglycerols of U.S. Pat. No. 3,988,446; compounds (A) are made from isopropylidene glycerol and for (C), one uses a labile glycerol monoester, e.g., the 2,2,2-trichloroethylcarbonate. Alternatively, (A) and (B) can be prepared from epichloro- or epibromohydrin, a method which is particularly advantageous for (B) when the two R° groups should be different.

In order to illustrate the present invention in more detail, reference is made to the following examples which, however, are not intended to limit the invention in any respect. In all instances, the described compounds were identified by matching microanalyses and by nmr, mass spectra and/or IR-spectra where the esters were liquids.

EXAMPLE 1

1,3-Dipalmitoyl-2-valproyl-glyceride (a) Dihydroxyacetone dimer is dried for 4 hours in a vacuum pistol at 50° C.; 13 g. of the dry material is suspended in 500 ml. of dry, ethanol-free chloroform in a one-liter round-bottomed three-neck flask equipped with a calcium chloride drying tube and a pressure-equalizing dropping funnel. To this suspension at 5° C. is added 25 ml. of dry pyridine. The mixture is cooled in an ice bath while 76 g. of freshly distilled palmitoyl chloride is added dropwise over one hour's time. The reaction mixture is stirred at room temperature overnight. The precipitate of pyridine hydrochloride is filtered off and the chloroform solution is washed with 100 ml. portions of water. The chloroform solution is then evaporated to give a gummy solid which is triturated with a small amount of diethyl ether and filtered to give 52.2 g. of a white solid identified as 1,3-dipalmitoyldihydroxyacetone, melting at 79°–82° C. and obtained in a yield of 64% of theory.

(b) In a three-liter Erlenmeyer flask, 50.2 g. of the above compound is suspended in 1100 ml. of tetrahydrofuran and 250 ml. of benzene using mechanical stirring. The mixture is cooled to 5° C. and 70 ml. of water is added. The mixture is stirred and 5.02 g. of neutral sodium borohydride (made by stirring commercial sodium borohydride in ethyl acetate overnight, washing with ether and drying) in 0.5 g. quantities is added followed by stirring the suspension at 5° C. for 45 minutes. At this time, 2.5 ml. of glacial acetic acid is added slowly to destroy excess borohydride and the mixture is stirred for 30 minutes at 5° C. before 300 ml. each of chloroform and diethyl ether are added. The mixture is washed with two 250 ml. portions of water and subsequently with 250 ml. of a 1% aqueous sodium bicarbonate solution. The organic layer is then dried over anhydrous magnesium sulfate and evaporated to give a gummy solid. This material is triturated with a small amount of acetone and filtered to give 44.4 g. (88%) of 1,3-dipalmitoylglycerol as a white solid melting at 71°–73° C.

(c) To a stirred solution of 9.04 g. of the above diester and 3.4 g. of pyridine in 40 ml. of dry carbon tetrachloride is added a solution of 6.36 g. of valproyl chloride in 20 ml. of carbon tetrachloride. Stirring is continued for 17 hours at room temperature and the insoluble salt is removed by filtration. The filtrate is evaporated to dryness and the residue is extracted with 200 ml. of petroleum ether (b.p. 30°–60° C.). The petroleum ether extract is washed in turn with 100 ml. of water, 100 ml. of 1% hydrochloric acid, 100 ml. of water and 100 ml. of brine, and dried over magnesium sulfate. Evaporation of the solvent leaves 3.8 g. of an oil which upon standing solidifies as 1,3-dipalmitoyl-2-valproyl-glyceride, m.p. 40°–42° C. (from pet. ether at 70° C.); mass spectrum m/e 692 (M$^+$ −42).

EXAMPLE 2

1,3-Didecanoyl-2-valproyl-glyceride

By following the procedure of Example 1(a) and (b) using 11.6 g. of dihydroxy acetone and 58.2 g. of didecanoyl chloride, 48.2 g. of 1,3-didecanoyloxy-2-propanol is obtained. Of this material, 6.42 g. is stirred for 17 hours at room temperature with 4.82 g. of pyridine and 7.82 g. of valproyl chloride in 30 ml. of dry carbon tetrachloride. The insoluble salt is filtered and the filtrate is evaporated to dryness. The residue is extracted with 200 ml. of petroleum ether (b.p. 30°-60° C.) and washed in turn with 100 ml. of water, 100 ml. 1% hydrochloric acid, 100 ml. of water and 100 ml. of brine, and then dried over magnesium sulfate. Removal of the solvent gives 11.49 g. of an oil which is purified by high pressure liquid chromatography to yield 3.2 g. of 1,3-didecanoyl-2-valproyl-glyceride; mass spectrum m/e 484 ($M^+ - 42$).

EXAMPLE 3

1,3-Dihexanoyl-2-valproyl-glyceride

By following the procedure of Example 1(a) and (b) using 7.21 g. of dihydroxyacetone and 22.9 g. of hexanoyl chloride, 1,3-dihexanoyloxy-2-propanol is obtained. The reaction of 7.04 g. of this material with 4.47 g. of valproyl chloride and 2.37 g. of pyridine as described in Example 1(c) yields an oil which is purified by chromatography on a column of silica gel (300 g. deactivated with wet ether). The triglyceride is eluted with petroleum ether/ether (85:15; b.p. 30°-60° C.) and treated with charcoal to produce 4.9 g. of 1,3-dihexanoyl-2-valproyl-glyceride. Mass spectrum m/e 372 ($M^+ - 42$).

EXAMPLE 4

1,3-Dibutanoyl-2-valproyl-glyceride

By following the procedure of Example 1(a) and 1(b) using 13.05 g. of 1,3-dihydroxyacetone, 23.7 g. of pyridine and 31.1 g. of butyryl chloride, 17.9 g. of 1,3-dibutanoyloxy-2-propanol is obtained. The reaction of 12.2 g. of this material and 9.4 g. of valproyl chloride and 4.98 g. of pyridine as described in Example 1(c) yields an oil which is purified by chromatography as described in Example 3. The pure 1,3-dibutanoyl-2-valproyl-glyceride is eluted from the column with petroleum ether/ether (95:5); it is obtained in a yield of 9.1 g.; $R_f$ 0.61 (petroleum ether/ether 3:1); mass spectrum m/e 316 ($M^+ - 42$).

EXAMPLE 5

1,3-Diacetyl-2-valproyl-glyceride

In analogy to the preceding examples, 13.68 g. of valproyl chloride is reacted with 1,3-diacetylglycerol which upon work-up as before yields 1,3-diacetyl-2-valproyl-glyceride as an oil which is purified by high pressure liquid chromatography to yield 4.2 g. of the desired pure ester; mass spectrum m/e 260 ($M^+ - 42$).

EXAMPLE 6

1-Valproyl-glycerol

A solution of 6.66 g. of valproyl chloride in 40 ml. of dry methylene chloride is added dropwise to a stirred solution of 5.29 g. of D,L-isopropylidene glycerol (known and marketed as Solketal) in 40 ml. of methylene chloride and 3 ml. of pyridine. The reaction mixture is stirred for 16 hours at room temperature and then treated with 50 g. of ice and 50 ml. of water. The organic layer is decanted, washed in turn with 100 ml. of water, 100 ml. of 5% hydrochloric acid solution, 100 ml. of water, 100 ml. of 5% aqueous sodium hydroxide and 100 ml. of water. After drying over sodium sulfate and solvent evaporation, 10 g. of an oil is obtained. This oil is dissolved in a mixture of 15 ml. of ether and 4 ml. of methanol and refluxed 17 hours with 4 ml. of 3N HCl. The cooled reaction mixture is then treated with 100 ml. of brine and dried over sodium sulfate. The solvent is evaporated and the residual oil is chromatographed over 300 g. of boric acid-impregnated Florisil, eluting 1-valproyl-glycerol with petroleum ether/ether 3:2. A yield of 61% of theory is obtained; mass spectrum m/e 187 ($M^+ - 31$).

The corresponding dialkanoyl esters of the described 1-valproylglycerol are obtained in well known fashion by simply esterifying this compound with at least 2 moles of a fatty acid acyl chloride or at least one mole of a fatty acid anhydride per mole of the shown glycerol.

EXAMPLE 7

1,3-Divalproylglyceride

By following the procedure of Example 1(a) and (b) using 39.3 g. of dihydroxyacetone and 142.4 g. of valproyl chloride, 148 g. of 1,3-divalproylglyceride is obtained. The crude product is purified by chromatography on a column of Florisil impregnated with boric acid (10%, w/w) and activated at 100° C. The diglyceride is eluted with petroleum ether (bp 30°-60° C.)/ether 95:5; $R_f$ 0.64 (petroleum ether/ether 50:50).

EXAMPLE 8

2-Acetyl-1,3-divalproylglyceride

By following the procedure of Example 1(c), 17.2 g. of 1,3-divalproylglyceride is stirred for 17 hours at room temperature with 4.8 g. of pyridine and 4.32 g. of acetyl chloride in 140 ml. of dry carbon tetrachloride. The reaction mixture is evaporated to dryness. The residue is extracted with 600 ml. of ether. The ether extracts are washed with 2×100 ml. of water, 100 ml. 1% hydrochloric acid, 100 ml. of water and 300 ml. of brine and then dried over magnesium sulfate. Removal of the solvent gives 18 g. of oil which is purified by high pressure liquid chromatography to yield 11.6 g. (60%) of 2-acetyl-1,3-divalproylglyceride. Mass spectrum m/e 344 ($M^+ - 42$).

EXAMPLE 9

2-Butanoyl-1,3-divalproylglyceride

By following the procedure of Example 8, 5.86 g. of butyryl chloride is reacted with 17.2 g. of 1,3-divalproylglyceride to give 9.2 g. (44%) of pure 2-butanoyl-1,3-divalproylglyceride. Mass spectrum m/e 372 ($M^+ - 42$).

EXAMPLE 10

2-Decanoyl-1,3-divalproylglyceride

By following the procedure of Example 8, 7.6 g. of decanoyl chloride is reacted with 12.5 g. of 1,3-divalproylglyceride to give the desired 2-decanoyl-1,3-divalproylglyceride. Mass spectrum m/2 456 ($M^+ - 42$).

EXAMPLE 11

1,2-Divalproylglyceride

A solution of 6.5 g. of valproyl chloride in 50 ml. of chloroform is added at 0° C. to a suspension of 5.35 g. of β, β, β-trichloroethylcarbonate glycerol in 3.32 g. of pyridine and 75 ml. chloroform. After 1 hour, the cooling bath is removed and the reaction mixture is stirred at room temperature for 18 hours before 400 ml. of ether is added to the reaction mixture. The organic layer is decanted, washed with 2×150 ml. of water, 2×150 ml. of 1% hydrochloric acid, 150 ml. of water, 2×150 ml. 1% aqueous sodium bicarbonate, 2×150 ml. water and 2×150 ml. of brine. The dried ether extracts (over sodium sulfate) are evaporated to dryness to yield an oil. This oil is dissolved in 100 ml. of ether and 65 ml. of glacial acetic acid is added, followed by cooling the mixture to 5° C. and then adding 15 g. of zinc dust to the stirred solution. Stirring is continued for 3 hours and 200 ml. of ether is added to the reaction mixture. The insoluble material is filtered and washed with ether. The ether extracts are washed as previously described and dried over magnesium sulfate. Removal of the solvent yields an oil which is chromatographed on 110 g. of Florisil. The obtained 1,2-divalproylglyceride is eluted with petroleum ether/ether 95:5. $R_f$ 0.56 (petroleum ether-ether) 50:50.

Simple esterification in accordance with the previous examples, using a fatty acid anhydride or halide produces the 1,2-valproylglyceride triesters of structure I wherein R and R' are valproyl and R" is a fatty acid acyl radical.

EXAMPLE 12

The compounds of the present invention were administered to mice and rats by oral intubation. A vehicle of 0.5% aqueous methylcellulose containing one drop of a polyethylene sorbitan monooleate was used to suspend the above compounds. In the case of Example 1, the compound was first ground in a tissue-homogenizer followed by mixing in a Waring blender. The results are shown in Table I expressed in mcg. of valproic acid per ml. of blood plasma at specified times. These results are the means of the concentrations of all 3-18 animals used in each group, each animal receiving the equivalent of 200 mg. of valproic acid.

TABLE I

| Compound of | Rats | | Mice | |
|---|---|---|---|---|
| Example # | 0.5 | 1.5 | 0.5 | 1.5 hrs. |
| 1 | 8.8 | 5.4 | 43.8 | 17.7 |
| 2 | 14.4 | 11.1 | 51.5 | 33.6 |
| 3 | 10.4 | 13.9 | 34.0 | 14.3 |
| 4 | 16.3 | 11.3 | 36.7 | 15.8 |
| 5 | 38.2 | 36.2 | 112.6 | 65.4 |
| 6 | 103.7 | 46.5 | 166.4 | 142.7 |
| 7 | 81.6 | 31.9 | 143.0 | 58.3 |
| 8 | 59.5 | 27.4 | 87.3 | 49.5 |
| 9 | 16.2 | 22.2 | 85.3 | 46.8 |
| 10 | 5.3 | 5.5 | 10.2 | 16.7 |
| Valproic Acid | 84.1 | 27.5 | 133.7 | 72.0 |
| Glycerol tri-valproate | 3.1 | 3.7 | 8.3 | 13.7 |

The above results demonstrate that significantly higher valproic acid blood levels are achievable with the new compounds over those of the trivalproate glyceride; however, with increasing alkyl length in the 1- and 3-positions of the 2-valproic acid glycerides or the 2-position of the 1,3-divalproic acid glycerides, the obtainable blood levels become lower.

EXAMPLE 13

In order to demonstrate the protective effects of the new compounds against audiogenic seizures, valproic acid, its 1-glyceride, the 1,3-diacetyl-2-valproylglyceride, and glyceride trivalproate were administered to male, albino mice which were genetically susceptible to sound induced seizures. The valproic acid equivalent of 800 mg./kg. of each compound was administered by oral intubation in a composition prepared as shown in Example 12 to groups of 10 mice. Thirty minutes after dosing, convulsions were produced by electrically activating a bell for one minute. The percentages of mice in each group exhibiting tonic extension seizures and any type of seizure are shown in Table II.

TABLE II

| | Percentage of Mice Exhibiting Seizures | |
|---|---|---|
| Compound | Tonic Extension | Any Type |
| Placebo | 90% | 100% |
| Glycerol tri-valproate | 80% | 100% |
| Valproic acid | 10% | 50% |
| Example 5 | 10% | 50% |
| Example 6 | 10% | 50% |

The new compounds provide seizure protection equivalent to that of valproic acid which is far superior to that provided by glycerol trivalproate.

EXAMPLE 14

Since it is possible that the new compounds are not absorbed as quickly as valproic acid itself, absorption profiles and area-under-the-curve (AUC) values were calculated for valproic acid, glyceride trivalproate and and representatives of the current compounds. The phrase AUC values represents the total quantity of the compound which is absorbed by the blood during the time periods referred to in Table III expressed in mcg./ml. A beagle dog received a single oral dose of 24.9 mg./kg. valproic acid equivalent in a composition prepared as shown in Example 12. The blood concentrations are shown in Table III as mcg./ml. while the AUC values are expressed as hr.×mcg./ml.

TABLE III

| Compound of | 0.5 | 1 | 2 | 4 | 6 hrs. | AUC for 8 hrs. |
|---|---|---|---|---|---|---|
| Example 5 | 27.9 | 42.7 | 15.2 | 4.1 | 0.4 | 74.1 |
| Example 6 | 58.2 | 45.1 | 12.6 | 2.7 | 0.9 | 87.9 |
| Example 7 | 5.7 | 10.2 | 5.4 | 1.4 | 0.7 | 21.9 |
| Valproic Acid | 65.6 | 40.8 | 9.0 | 2.6 | 1.3 | 82.2 |
| Glycerol tri-valproate | 0.5 | 0.4 | 0.0 | 0.0 | 0.0 | 0.6 |

The new compounds clearly exhibit absorption profiles similar to valproic acid. The new compounds also demonstrate AUC's which are far greater than the AUC of the previously known trivalproylglyceride.

EXAMPLE 15

The equivalent of 300 mg. of valproic acid of the compounds of Examples 4, 5 and 7 as well as 300 mg. of valproic acid were individually homogenized in 0.5% aqueous methylcellulose containing two drops of polyethylene sorbitan mono-oleate per 10 ml. These formulations were administered by oral intubation to groups of rats which had been fasted 18-20 hours before this experiment. Four hours after dosing, the animals were killed and the gastric mucosa were examined for lesions. The results shown in Table IV represent the number of animals showing gastric lesions vs. the number of animals in each group.

TABLE IV

| Valproic acid | 20 in 36 |
|---|---|
| Example 4 | 1 in 10 |
| Example 5 | 0 in 6 |
| Example 7 | 1 in 10 |
| Control | 0 in 10 |

The results show the almost complete elimination of gastro-intestinal irritation with the new componds when orally administered at the same dose equivalent as valproic acid.

The glycerides of the present invention are pharmaceutically as effective in the same fashion as valproic acid or its sodium salt; however, the new esters are far superior to the free acid or salt from the standpoint of oral acceptability. The new esters are essentially free of gastro-intestinal side effects, causing essentially no irritation, stomach upsets or lesions. The latter was easily demonstrated with an animal model known to have characteristics and sensitivities similar to humans.

Therapeutic orally useful compositions containing the esters of the current invention preferably contain between 0.3 and 7 millimoles of the active material, valproic acid. The ester can be administered in capsule form or together with a pharmaceutically acceptable solid carrier or diluent. Such dosage forms may be prepared as pills, wafers, or tablets. Liquid dosage forms may also be used and for pediatric or geriatric patients, they may be preferred. The new esters may be suspended in water, syrup, or the like in a fashion well known to those skilled in the art, using common, pharmaceutically acceptable coloring agents, flavoring agents and suspending agents.

For solid dosage forms, standard tableting procedures can be used. An amount equivalent to 0.66 gram moles and 50 g. of cornstarch are blended until homogeneous and passed through a 40-mesh screen. This blend is granulated with a solution of 15 g. of polyvinylpyrrolidone in alcohol or water and subsequently dried in a hot-air oven at 50° C. After sifting through a 16-mesh screen, the granules are thoroughly blended with 10 g. of talcum powder, 2.5 g. of magnesium stearate, 1.0 g. of combined coloring and flavoring agents, and passed through a 30-mesh screen. This blend is compressed into 1000 tablets using a ⅜" standard round punch resulting in a hardness of 7-9, each tablet containing $0.66 \times 10^{-3}$ gram moles of the active material.

The protective effect afforded by administration of the compounds is substantially identical to that obtained with the same amount of valproic acid. However, with te significant improvement obtained in respect to gastro-intestinal problems created by valproic acid itself, the esters of the present invention are far superior to valproic acid for the control of convulsion or seizures in epileptic patients.

We claim:

1. A glyceride of the formula

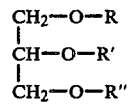

wherein R, R', R and R' or R and R" represent valpropyl and the remaining substituent or substituents are hydrogen or a fatty acid acyl radical of formula X—CO— wherein X is a non-valpropyl alkyl group of 1-15 carbon atoms with the proviso that when R' is valproyl, R and R" both are represented by X—CO—.

2. A glyceride of claim 1 wherein R' is valproyl and R and R" are X—CO—.

3. The glyceride of claim 2 wherein X is methyl.

4. The glyceride of claim 2 wherein X is pentyl.

5. A glyceride of claim 1 wherein R is valproyl.

6. The glyceride of claim 5 wherein R' and R" are H.

7. A glyceride of claim 5 wherein R' and R" are X—CO—.

8. The glyceride of claim 7 wherein X is methyl.

9. The glyceride of claim 7 wherein X is propyl.

10. The glyceride of claim 1 wherein R and R" are valproyl and R' is H.

11. A pharmaceutical composition in oral dosage form for the control of convulsion or seizures, containing as the active principle an amount of sufficient to control or reduce convulsion or seizures of a glyceride of the formula

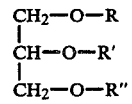

wherein R, R', R and R' or R and R" represent valproyl and the remaining substituent or substituents are hydrogen or a fatty acid radical of formula X—CO— wherein X is a non-valpropyl alkyl group of 1-15 carbon atoms with the proviso that when R' is valproyl, R and R" both are represented by X—CO—, together with a pharmaceutically acceptable diluent.

12. The composition of claim 11 wherein said diluent is a solid.

13. The composition of claim 12 in tablet form.

14. A composition of claim 11 wherein R' is valproyl and R and R" are X—CO—.

15. The composition of claim 14 wherein X is methyl.

16. The composition of claim 14 wherein X is pentyl.

17. A composition of claim 11 wherein R is valproyl.

18. The composition of claim 17 wherein R' and R" are H.

19. A composition of claim 17 wherein R' and R" are X—CO—.

20. The composition of claim 19 wherein X is methyl.

21. The composition of claim 19 wherein X is propyl.

22. The composition of claim 11 wherein R and R" is valproyl and R' is H.

23. A pharmaceutical composition in oral dosage form for the control of convulsion or seizures containing as the active principle a glyceride of the formula:

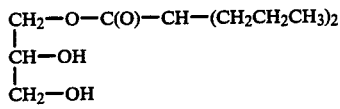

with a pharmaceutically acceptable diluent.

24. A pharmaceutical composition for treating convulsive states and seizures, which comprises as essential active ingredient in amounts sufficient to control or reduce convulsions or seizures, at least one glyceryl ester selected from the group consisting of glyceryl 1,2-bis-(di-n-propylacetate) and glyceryl 1,3-bis-(di-n-propylacetate), in combination with a pharmaceutical carrier or excipient therefor.

25. A method of treating convulsive states and seizures in a human being in need of such treatment, which comprises administering to said human being a therapeutically effective dose of a glyceryl ester selected from the group consisting of glyceryl 1,2-bis-(di-n-propylacetate) and glyceryl 1,3-bis-(di-n-propylacetate).

* * * * *